US012150730B2

(12) United States Patent
Yip et al.

(10) Patent No.: US 12,150,730 B2
(45) Date of Patent: Nov. 26, 2024

(54) HANDHELD FLEXIBLE ROBOTIC CATHETER FOR ENDOSCOPIC INSTRUMENTATION

(71) Applicant: The Regents of the University of California, Oakland, CA (US)

(72) Inventors: Michael Yip, La Jolla, CA (US); Phillip Weissbrod, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 82 days.

(21) Appl. No.: 17/307,649

(22) Filed: May 4, 2021

(65) Prior Publication Data
US 2021/0338355 A1    Nov. 4, 2021

Related U.S. Application Data

(60) Provisional application No. 63/019,621, filed on May 4, 2020.

(51) Int. Cl.
*A61B 1/00* (2006.01)
*A61B 1/005* (2006.01)
(Continued)

(52) U.S. Cl.
CPC .......... *A61B 34/74* (2016.02); *A61B 1/00105* (2013.01); *A61B 1/0052* (2013.01); *A61B 1/0057* (2013.01); *A61B 1/018* (2013.01); *A61B 1/05* (2013.01); *A61B 34/35* (2016.02); *A61B 2017/00424* (2013.01); *A61B 2034/301* (2016.02); *A61B 2034/742* (2016.02); *A61M 25/0026* (2013.01); *A61M 25/0136* (2013.01)

(58) Field of Classification Search
CPC . A61B 1/00105; A61B 1/0052; A61B 1/0057; A61B 1/018; A61B 1/05; A61B 34/74; A61B 34/35; A61B 2034/301; A61B 2034/742; A61B 2017/0034; A61B 2017/2925; A61B 34/30; A61B 1/0051
See application file for complete search history.

(56) References Cited

U.S. PATENT DOCUMENTS 5,052,402 A    10/1991  Bencini
11,547,509 B2 *  1/2023  Gunn ................ A61M 25/0026
(Continued)

FOREIGN PATENT DOCUMENTS

WO    WO-2019070696 A1 *  4/2019  ........... A61B 1/0051

*Primary Examiner* — Anh Tuan T Nguyen
*Assistant Examiner* — Rynae E Boler
(74) *Attorney, Agent, or Firm* — Stuart H. Mayer; Kaplan Breyer Schwarz LLP

(57) ABSTRACT

A handheld, steerable catheter robotic system includes a catheter having a flexible outer sheath, at least one flexible multi-lumen assembly and a robotic instrument for performing a surgical procedure. The catheter is removably insertable into an instrument channel of an endoscope. The flexible multi-lumen assembly extends through the outer sheath. The robotic instrument is operatively and removably attachable to a distal end of the multi-lumen assembly such that the robotic instrument is teleoperable. The catheter robotic system also includes a handle operatively and removably attachable to a proximal end of the catheter. The handle is configured for hand-held operation and includes a joystick for steering the robotic instrument.

18 Claims, 14 Drawing Sheets

(51) Int. Cl.
*A61B 1/018* (2006.01)
*A61B 1/05* (2006.01)
*A61B 34/00* (2016.01)
*A61B 34/35* (2016.01)
A61B 17/00 (2006.01)
A61B 34/30 (2016.01)
A61M 25/00 (2006.01)
A61M 25/01 (2006.01)

(56) References Cited

U.S. PATENT DOCUMENTS

| | | | |
|---|---|---|---|
| 12,011,246 B2 * | 6/2024 | Gunn | A61B 34/30 |
| 2005/0065399 A1 * | 3/2005 | Sasaki | A61B 1/018 |
| | | | 600/153 |
| 2005/0096502 A1 | 5/2005 | Khalili | |
| 2006/0183975 A1 | 8/2006 | Saadat | |
| 2009/0054733 A1 | 2/2009 | Marescaux | |
| 2009/0216077 A1 * | 8/2009 | Banju | A61B 1/018 |
| | | | 600/106 |
| 2010/0137681 A1 | 6/2010 | Ewers | |
| 2011/0160532 A1 | 6/2011 | Heimberger | |
| 2011/0288536 A1 | 11/2011 | Dejima | |
| 2012/0253116 A1 * | 10/2012 | Sniffin | A61B 1/008 |
| | | | 600/106 |
| 2015/0250546 A1 | 9/2015 | Larkin et al. | |
| 2016/0128547 A1 * | 5/2016 | Ogawa | A61B 1/00006 |
| | | | 600/107 |
| 2016/0183772 A1 * | 6/2016 | Hatta | A61B 1/00133 |
| | | | 600/106 |
| 2017/0071687 A1 | 3/2017 | Cohen et al. | |
| 2017/0079674 A1 * | 3/2017 | Collings | A61B 17/2909 |

\* cited by examiner

HANDHELD FLEXIBLE ROBOTIC CATHETER FOR ENDOSCOPIC INSTRUMENTATION

CROSS-REFERENCE TO RELATED APPLICATIONS

This application claims the benefit of U.S. Provisional Application Ser. No. 63/019,621, filed May 4, 2020, the contents of which are incorporated herein by reference. This application is also related to U.S. Ser. No. 16/652,968, filed Apr. 1, 2020 entitled "STEERABLE CATHETER FLEXIBLE ROBOTIC SYSTEM FOR USE WITH ENDOSCOPES".

BACKGROUND

Robotic surgical instrumentation as applied to endoscopic procedures is an evolving landscape. In general, the integration of robotics into endoscopic intervention refers to the utilization of robotic instrumentation with endoscopic visualization. This potentially allows for the enhancement of current procedures with respect to quality, user experience, and/or operative time. The technology may also allow new procedures to be performed.

The control mechanisms for these robotic devices tend to be bulky, separate from the endoscope, and typically require multiple users to drive the scope and operate the robot simultaneously. Currently proposed systems are either complete systems inclusive of both robotic arms and imaging, or devices that are supplemental and only provide robotic instrumentation.

SUMMARY

In accordance with one aspect of the present disclosure, the working channel of an endoscope is used to deliver robotic technology. Delivery of a robotic catheter via a working channel allows for application of numerous different technologies. In particular, the catheter acts as a conduit (i.e., it is hollow) to allow the passage of a variety of instruments including laser fibers, cup forceps, baskets, loops, applications of clips/suture, or other energy delivery devices. The catheters are disposable and vary in length and diameter depending on the application and the size of the working channel they pass through.

In accordance with one particular embodiment, a handheld, steerable catheter robotic system includes a catheter having a flexible outer sheath, at least one flexible multi-lumen assembly and a robotic instrument for performing a surgical procedure. The catheter is removably insertable into an instrument channel of an endoscope. The flexible outer sheath has a proximal end and a distal end. The flexible multi-lumen assembly extends through the outer sheath. The multi-lumen assembly has a proximal end and a distal end. The robotic instrument is operatively and removably attachable to the distal end of the multi-lumen assembly such that the robotic instrument is teleoperable. The catheter robotic system also includes a handle operatively and removably attachable to a proximal end of the catheter. The handle is configured for hand-held operation and includes a joystick for steering the robotic instrument.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

As described in more detail below, a steerable catheter robotic system with a significantly reduced size-footprint is provided for deployment in field or outpatient pulmonary surgical procedures. The small size and portability of this system can help overcome a major disadvantage of current surgical robots which take up an immense amount of space in already crowded-operating rooms, while still being able to imitate, copy and improve human capabilities. In some embodiments the dimensions of the robotic instruments or tools may be as small as 1 mm.

Figure 1:
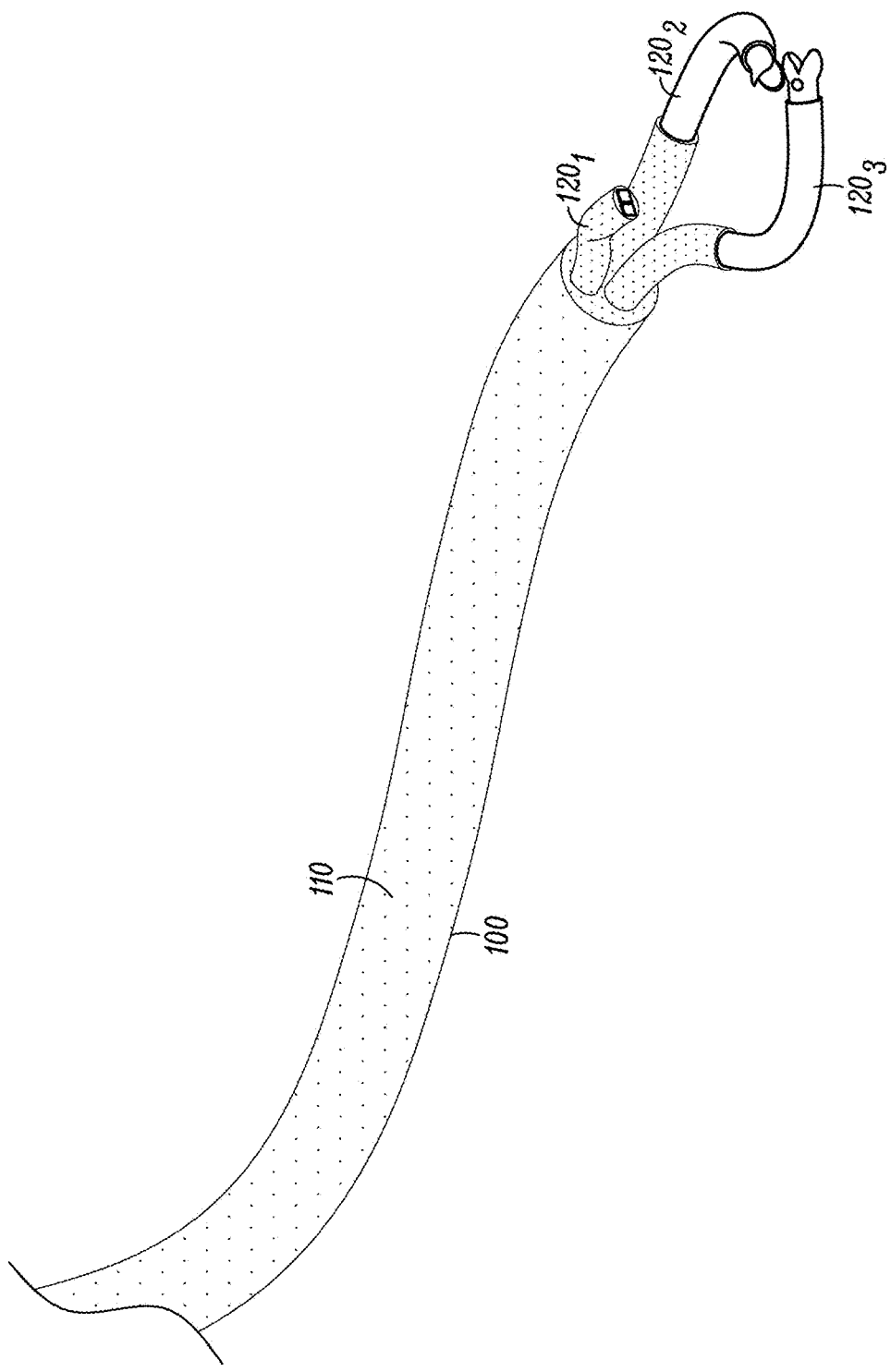
FIGS. 1 and 2 show perspective views of a multi-catheter subsystem.
Figure 2:
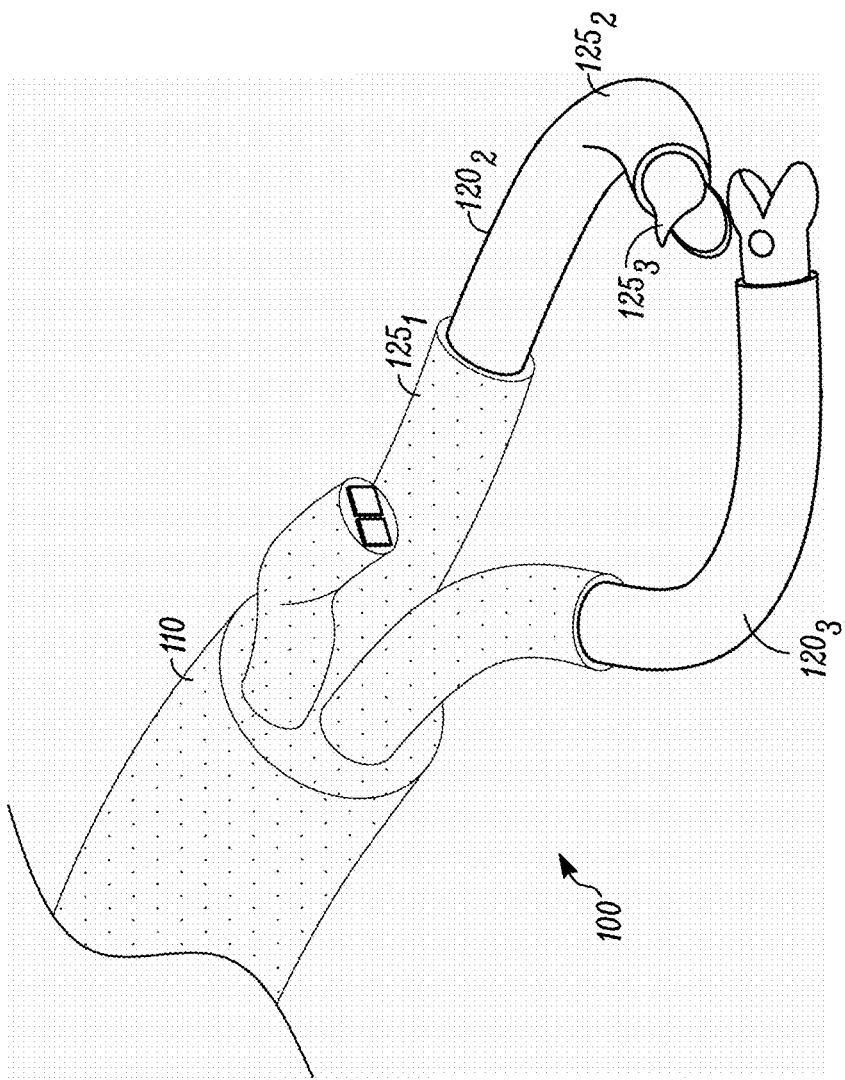

FIGS. 1 and 2 show perspective views of a multi-catheter subsystem 100 that includes a flexible outer guide shaft 110 having a distal end from which one or more robotic instruments extend. Although the embodiment shown in FIGS. 1 and 2 shows three robotic instruments $120_1$, $120_2$ and $120_3$ ("120"), more generally any number of such robotic instruments 120 may be employed. In this particular embodiment the robotic instruments 120 include a camera $120_1$ and first and second grasping forceps $120_2$ and $120_3$. A control assembly (not shown in FIGS. 1 and 2) is located at the proximal end of the outer sheath 110 controls the operation of the robotic instruments 120.

In some embodiments each robotic instrument 120 may include two or more articulating segments that provide the instrument with multiple degrees of freedom. For instance, as best seen in FIG. 2, the first grasping forcep $120_2$ includes three articulating segments 1251, 1252 and 1253. The second grasping forcep $120_3$ may be similarly configured. By employing a suitable number of articulating segments, some instruments may be supplied with 7 degrees of freedom of articulation (i.e. positional control of x, y, z in cartesian space, and roll-pitch-yaw in orientation, and an actuation degree of freedom such as a pinch grip of a forcep), thereby essentially recovering the dexterity of a human hand. In such an embodiment a one-to-one mappings can be advantageously realized of a teleoperating using to the robotic instrument. If more than 7 degrees of freedom are provided to a given instrument, the instrument can have additional degrees of freedom to conform to the environment without affecting the controllability of the 7 degrees of freedom that are controlled by the human operator. Some instruments may have additional elbow deflection locations that allow the shape of the instrument to better conform to the environment.

When one of the robotic instruments is a camera, it may be operated with only 6 degrees of freedom for full visual control, although the focal depth (if so integrated) may be considered a $7^{th}$ degree of freedom.

Figure 3:
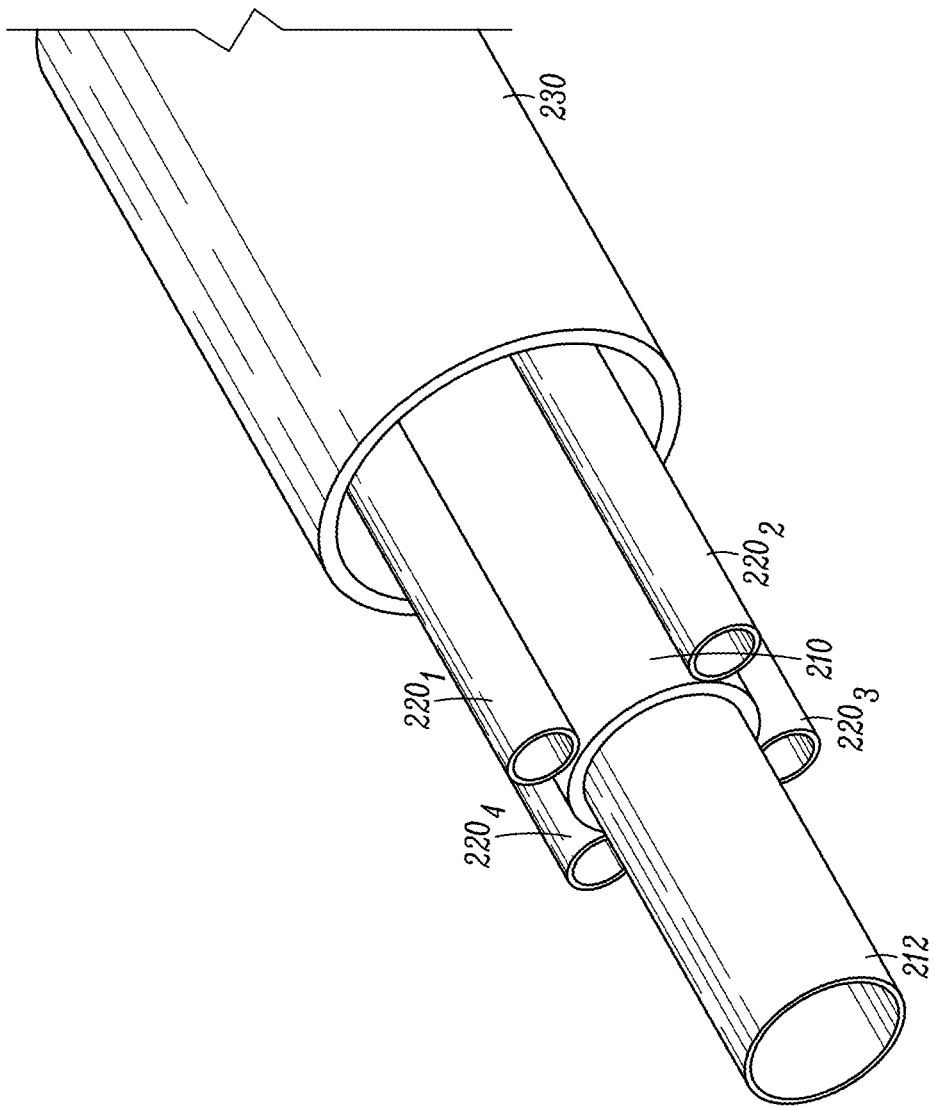
FIG. 3 shows one example of a multi-lumen assembly that is used to steer a single one of the robotic instruments shown in FIGS. 1 and 2.

FIG. 3 shows one example of a multi-lumen assembly 200 that is used to steer a single instrument 120. Each of the lumens is formed from a flexible material such as a flexible polymer. The multi-lumen assembly 200 extends through the outer guide shaft 110 shown in FIG. 1. The multi-lumen assembly 200 includes a center channel 210 that has a liner 212 that serves as an instrument port for one segment of a multi-segment instrument (or a complete instrument of a single-segment instrument). Surrounding the center channel 210 are a series of control lumens 220 through which articulation wires (not shown) extend. In this example 4 control lumens 2201, 2202, 2203 and 2204 are shown. The control lumens 220 are secured (e.g., fused) to the center channel 210. Articulation of the instrument segment located in the center channel 210 is determined by the coordinated operation of the articulation wires via the control assembly, which will be described below. The center channel 210 and the control lumens 220 may extend through a flexible sheath 230 (which itself extends through the outer guide shaft 110 shown in FIGS. 1 and 2).

Each articulating segment of a multi-segment instrument includes its own dedicated multi-lumen assembly 200 for controlling that segment. The different multi-lumen assemblies 200 of a single multi-segment instrument may be concentrically arranged with one another.

As mentioned above, the multi-lumen assembly 200 may be fabricated from flexible polymers. For example, in some embodiments the flexible sheath 230 and center channel 210 may be formed from a varying durometer thermoplastic polymer such as a polyester block amide (available, for instance, under the tradename PEBAX®). An optional stainless steel or fiber braid (not shown) may surround the flexible sheath 230. Likewise, in some embodiments the control lumens may be formed polymide and the liner 212 lining the center channel 210 may be formed from PTFE (i.e., Teflon®). The use of flexible polymers for the multi-lumen assembly affords significant flexibility in short segments without deterioration of the assembly and tight radiuses of curvatures can be achieved. Lamination of these polymers, which can become micron-thickness layers, enables these robotically controlled lumens to reach as small as 1 mm in diameter.

Figure 4:
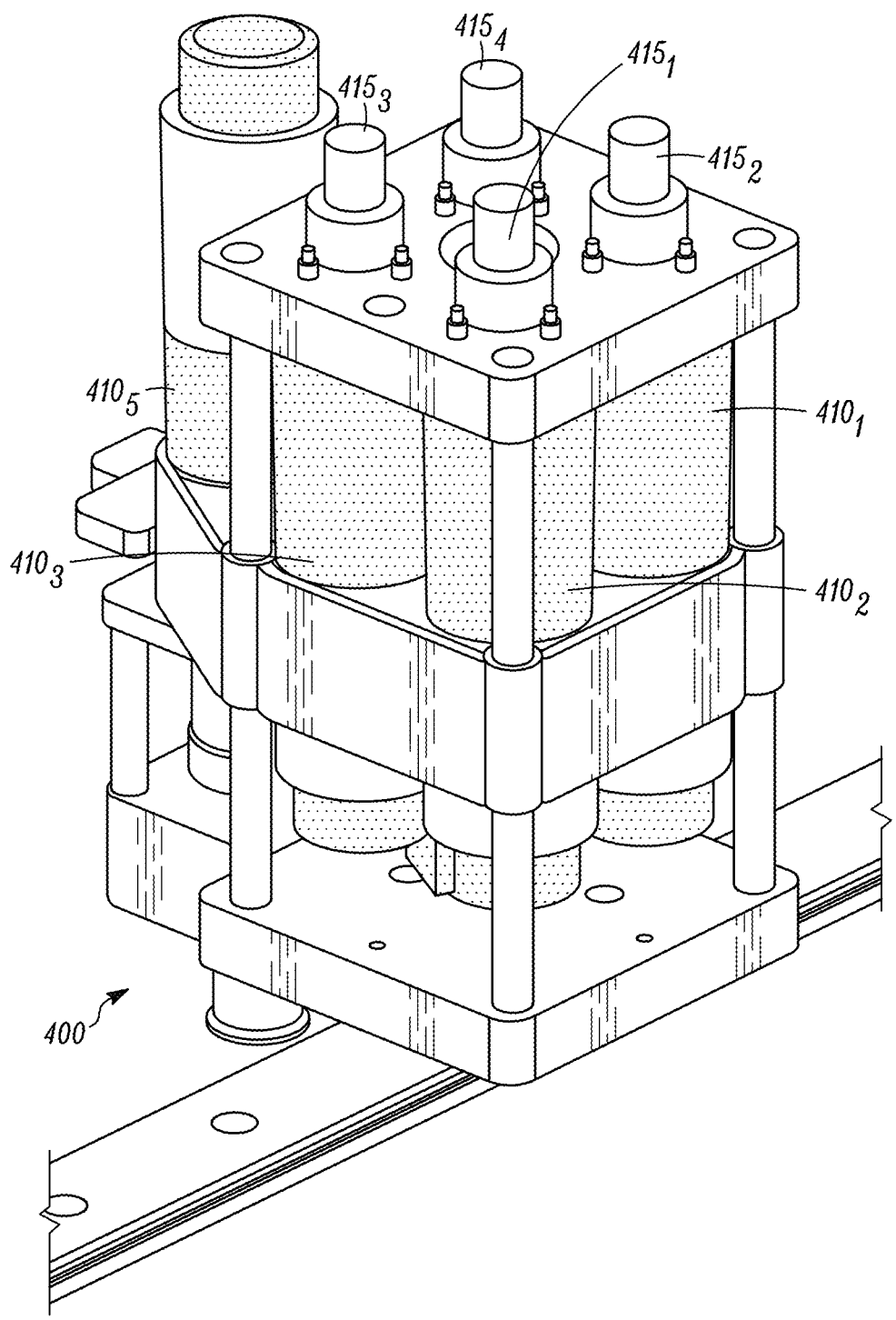
FIG. 4 shows a motor control assembly.
Figure 5:
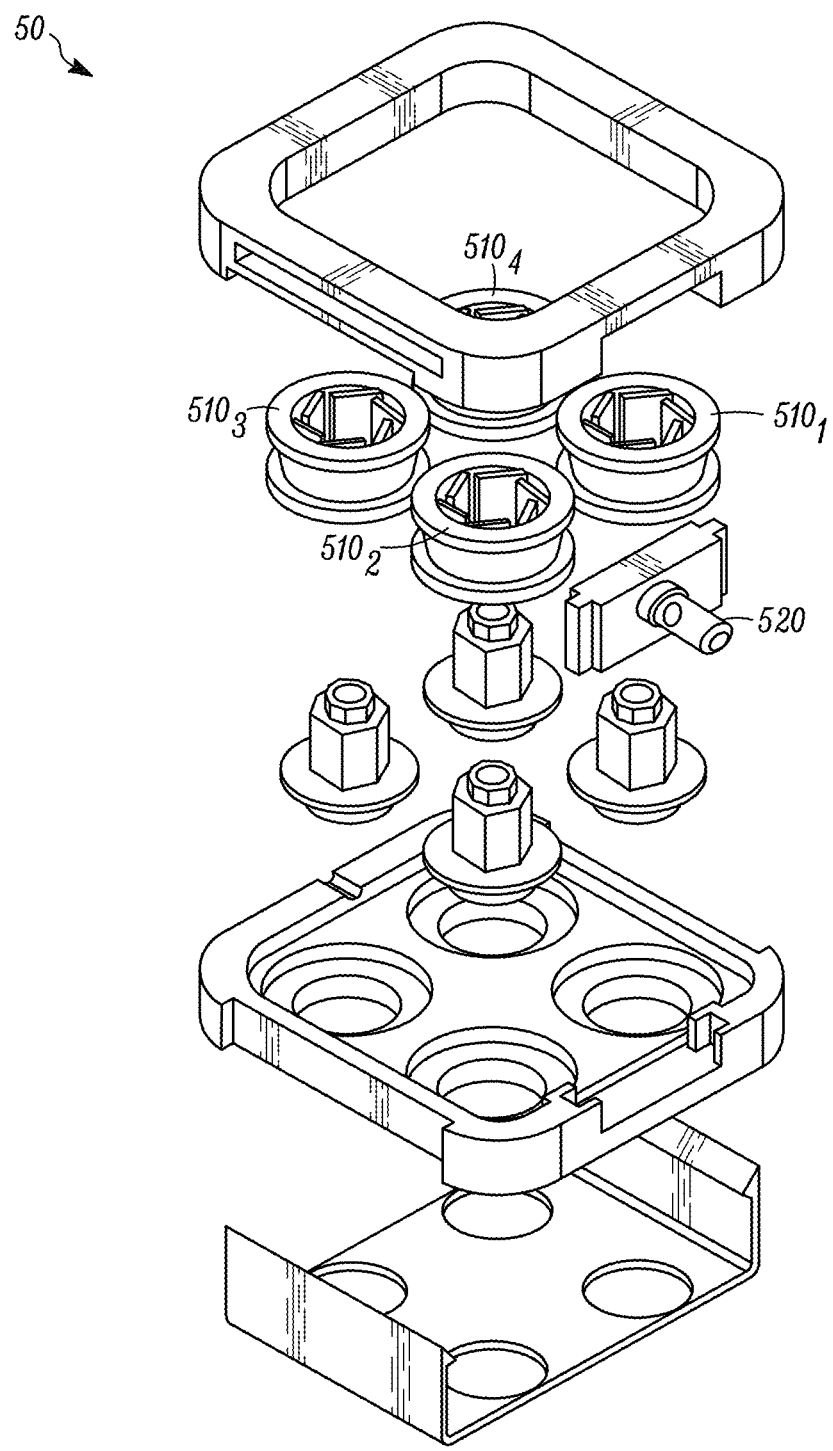
FIG. 5 shows a pulley housing assembly.

FIG. 4 shows a motor control assembly 400 that can be used in conjunction with a pulley housing assembly 500 (FIG. 5) to control the four pull wires that extend through the control lumens 220. The motor control assembly 400 includes four motors 4101, 4102, 4103 and 4104 (where motor 4104 is not visible in FIG. 4). that each respectively control the rotation of a rotatable shaft 4151, 4152, 4153 and 4154. The pulley housing assembly 500 includes four torque-limiting pulleys 5101, 5102, 5103 and 5104. As seen in FIG. 5, torque-limiting is accomplished using a two-part pulley, where the two parts are concentrically assembled (FIG. 5 shows them prior to assembly). The interface between the two parts is a flexure that can slip if too much torque is applied. When the pulley housing assembly 500 is mated with the motor control assembly 400 each pulley 5101, 5102, 5103 and 5104 is axially mounted on one of the shafts 4151, 4152, 4153 and 4154. The pulley housing assembly 500 also includes a shaft mount 520 onto which is mounted the outer guide shaft 110 and the multi-lumen assemblies 200 extending therethrough. Once installed, rotational actuation of the motors 410 located in the motor control assembly 420 is translated to linear actuation, providing four degrees of freedom to each instrument segment.

The motor control assembly 400 includes an additional motor 4105 that is used to extend and retract the robotic instrument under its control.

The control of the robotic instruments is accomplished using inverse kinematics to map Cartesian coordinates into the positions of the four pull wires. Coordinates are first multiplied by a dynamically adjustable rotation matrix, and then by constants derived during a simple calibration process in order to standardize actuation across multiple instruments. A position-based control approach using analog values to scale targets in Cartesian space that are then mapped to $R^4$, resulting in high position accuracy along with precise control over actuation velocity. The final result is accurate and intuitive control over two degrees of freedom per instrument, all mapped to a user interface.

More specifically, the exact mapping between a deflection and the amount of displacement of the articulation wires is a nonlinear mapping, $$x(s)=f(q_1,q_2,\ldots q_m)$$

where x represents a distal deflection specified as the curvature from proximal (0) to distal(s) end, (s: 0→total_length), and $q_1 \ldots q_m$ represents the displacements of m wires. The nonlinear mapping f may be known a-priori based on geometric or mechanic reasoning, or the mapping may be found using a regression strategy (such as a least-squares fit, or neural network approach). With the mapping, a desired shape x(s) may be found by taking the inverse mapping $f^{-1}$ which can be found either analytically, if possible, or empirically using gradient descent.

$$q_1,\ldots q_m=f^{-1}(x(s))$$

This mapping and inverse mapping may be performed by any suitable processor.

Figure 6:
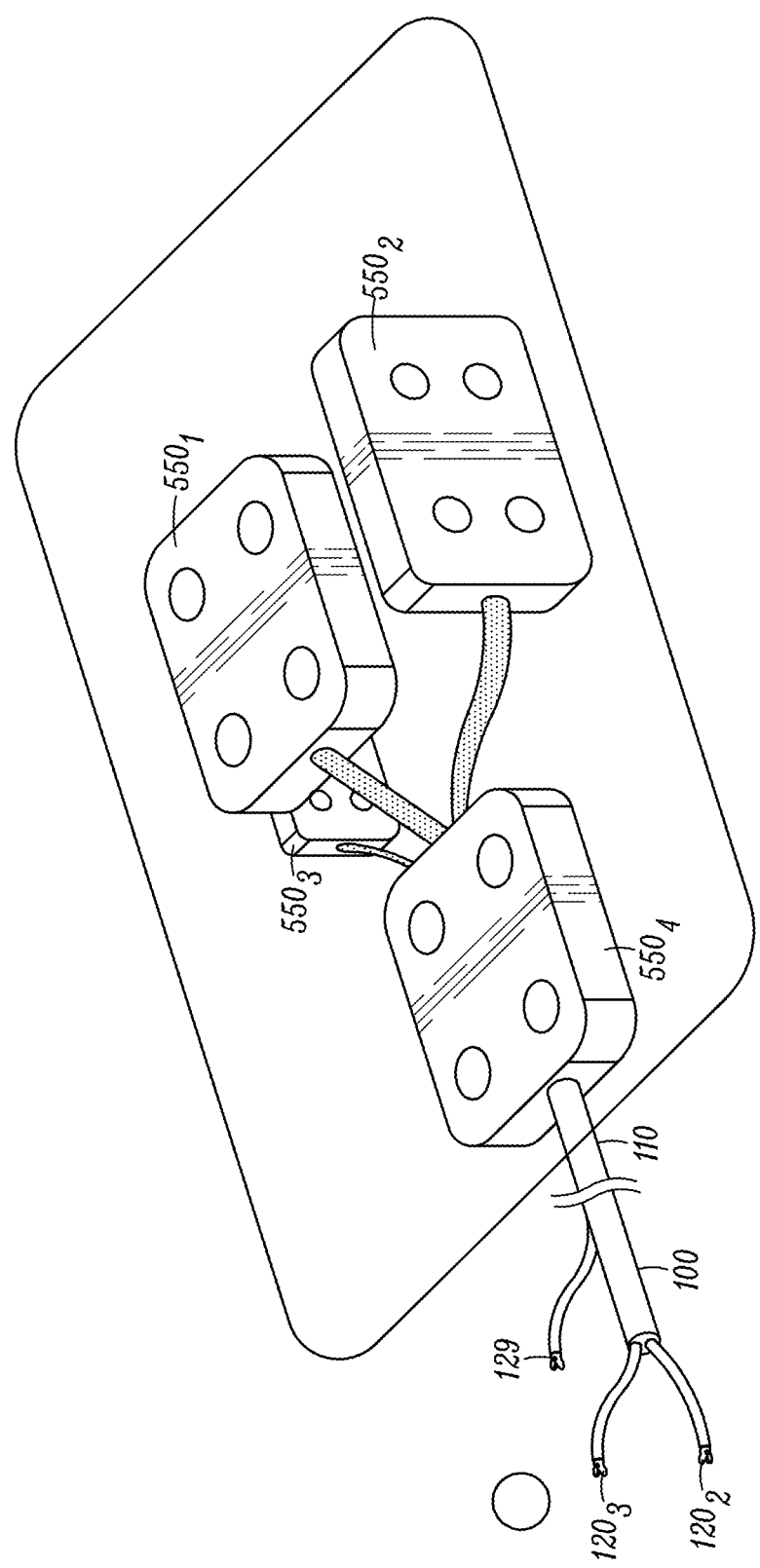
FIG. 6 shows an example of a steerable catheter robotic system that includes the multi-catheter subsystem shown in FIGS. 1 and 2.

FIG. 6 shows an example of the steerable catheter robotic system that includes the multi-catheter subsystem 110 shown in FIGS. 1 and 2, which includes the three instruments $120_1$, $120_2$ and $120_3$. Like reference numerals shown in FIG. 6 and the remaining figures denote like elements. As shown, the proximal end of the multi-catheter subsystem 110 includes controllers $550_1$, $550_2$, $550_3$ and $550_4$ ("550"). Each controller 550 includes one of the motor control assemblies 400 mated with one of the pulley housing assemblies 500. Controller $550_1$ is used to control instrument $120_1$, controller $550_2$ is used to control instrument $120_2$ and controller $550_3$ is used to control instrument $120_3$. The additional controller $550_4$ is used control the overall movement of the multi-catheter subsystem 110.

Control of the steerable catheter robotic system via a user interface (not shown) focuses on two distinct tasks: robot movement and multiple catheter articulation. Both movements can be controlled from a single console. For instance, in one embodiment the operator is able to advance the robot via a haptic joystick. The path of the multi-catheter subsystem can be visualized on a display of the user interface console. The display may include a high-definition or 3-D screen. Additional screens within the console may allow for projection of imaging studies or electromagnetic instrument registration for use during the procedure being performed. The joystick allows forward and backward movement and 180° movement in an x and y plane of the distal tip. To prevent traumatic navigation, haptic feedback may be provided which is associated with the platform movement. Once positioned in the desired location, the platform can be fixed to allow stability during instrument insertion and movement.

In some cases the desired path to be traversed by the catheter robotic system may be specified by the operator using a component of the user interface (e.g., a joystick, mouse, drawing pad). This information is used as input to the above-mentioned inverse mapping process and the results are delivered to the motors that drive the articulation wires in the catheter robotic system. In other circumstances, instead of specifying the path to be traversed by the catheter robotic system, it may be desirable to specify the final distal position of the catheter and allow the processor to resolve the path that should be followed to reach that final position.

As discussed above, in one embodiment there are two articulating instruments that can be inserted through the length of the multi-catheter subsystem. Movement of each instrument is controlled by independent finger grasping interfaces. The instruments can be advanced or withdrawn by depression or retraction of a grasping unit. In instances where there are no grasping movements, the instruments may be moved as if grasping a virtual pencil.

A wide variety of different interchangeable robotic instruments may be used in the multi-catheter subsystem. Examples of such instruments include, without limitation, biopsy cups, grasping forceps, injection needles, biopsy needles, laser introducers, basket retrievers, hot knives, clip appliers, and scissors. The instrument or instruments that are used will be application-dependent. Examples of such applications include laryngeal, pharyngeal, hypopharyngeal, tracheal, bronchial, esophageal, stomach, large and small bowel applications. Additionally, applications include newer advanced endoscopic procedures, including endoluminal tumor ablation in varying anatomic locations, Peroral Endoscopic Myotomy (POEM), and Natural Orifice Transluminal Endoscopic Surgery (NOTES).

Robotic instruments may be interchangeable so that the multi-catheter subsystem 100 can swap the types and locations of instruments as required to generate different configurations for a user to extend their ability to work with tissues in a narrow space, extend their reach, improve their visual range, or improve the ergonomics of control. The software controlling the multi-catheter sub-system may reposition its coordinate frame to match an intuitive viewpoint of the teleoperator.

In some cases it is possible that the system can introduce more robotic instruments than a single user can control. In this scenario, both a primary user and an assistant may operate different instruments through the same system, enabling multiple robotic instruments to be controlled simultaneously. This encourages shared tasks, allowing assistants to help with the retraction of objects or environmental roadblocks while the primary user is operating on the exposed area.

One embodiment of the system may involve the autonomous control of one instrument that follows or performs some assistive task that follows the behavior of a primary user. For example, a continuous ablation using a laser that reaches deeper within a site may be realized by having one of the robotic instruments follow a user-controlled ablation probe as it moves through the environment, i.e., a robotically controlled camera. In this case one instrument would be teleoperated while the other is autonomous and following the teleoperated camera.

The ability to simultaneously control and steer multiple robotic instruments can provide critical capabilities in manipulating areas of tissues with bimanual manipulation. For example, controlled stretching of tissue or peeling of tissue can be achieved only with two or more instruments. Likewise, the ability to mount and control a camera independently of the other instruments (and vice-versa) is a significant advantage over current endoscopic approaches where the endoscope is the camera and dictates the controllability of the instruments exiting from its orientation-fixed instrument lumen. Moreover, the multi-catheter system may be mixed with manual instrumentation given that the instrumentation fits within the available lumens for control.

Another advantage of the steerable catheter robotic system described herein is that one of its intracorporeal instruments can be used to stabilize another when there is a desire for improved stiffness. For example, an outstretched robotic instrument may become too compliant to lift a tissue that is far away. A support provided from a second robotic instrument may be devised to generate mechanical leverage that can amplify the force generation or the reachability of the original, unsupported instrument. In the same way, the robotic instruments may be used to support the sub-system in general and create anchors to provide stabilization against patient or anatomical motions or more generally to combat moment-arm effects.

Yet another advantage of the steerable catheter robotic system described herein arises in those embodiments that are fabricated exclusively from polymer or other non-metallic materials since these embodiments may be used in conjunction with magnetic resonance imaging (MRI) techniques.

In some embodiments, the steerable catheter robotic system is configured to be delivered through the working or instrument channel of a wide variety of different endoscopes. Such endoscopes can provide a way to navigate tortuous native patient cavities, but require a certain level of rigidity and size, making them less than ideal to navigate within small spaces once a surgical site is reached. Conventional tools and instruments that are designed to pass through conventional instrument channels of an endoscope are often more flexible, but generally only axial motion is controllable. By using the steerable catheter robotic system described herein, a substantial increase in instrument dexterity and reach can be achieved, while minimizing costs and equipment traditionally associated with robot-assisted procedures. The added dexterity provided to the operator while working in a very limited space results in a substantial broadening of the types of procedures that can be performed through a flexible endoscope. Moreover, the robotic steering of small caliber tools enables access to deeper anatomic structures than has previously been possible.

In order to be used in an endoscope, the steerable catheter robotic system needs to have a sufficiently small diameter so that it fits through conventional instrument channels. To accomplish this it will generally be necessary to limit the number of robotic instruments that may be used in the steerable catheter robotic system. For instance, in some cases the steerable catheter robotic system may be limited to only a single robotic instrument with 1 or 2 segments. Such a system will generally be able to be accommodated through the instrument channel of most typical endoscopes.

In use, the steerable catheter robotic system may be sufficiently light that the entire assembly, including the motor control assembly and the pulley housing assembly, may be handheld. In other cases the steerable catheter robotic system may be clamped or otherwise secured to an articulating support arm to support its weight.

There are many types of endoscopes, and they are generally named in relation to the organs or areas with which they are used. For example, gastroscopes are used for examination and treatment of the esophagus, stomach and duodenum; colonoscopes for the colon; bronchoscopes for the bronchi; laparoscopes for the peritoneal cavity; sigmoidoscopes for the rectum and the sigmoid colon; arthroscopes for joints; cystoscopes for the urinary bladder; and angioscopes for the examination of blood vessels. Embodiments of the steerable catheter robotic system shown herein may be used in conjunction with any of these different types of endoscopes. Moreover, the steerable catheter robotic system is not limited to medical applications but may be used in conjunction with other types of endoscopes such as borescopes.

Figure 7:
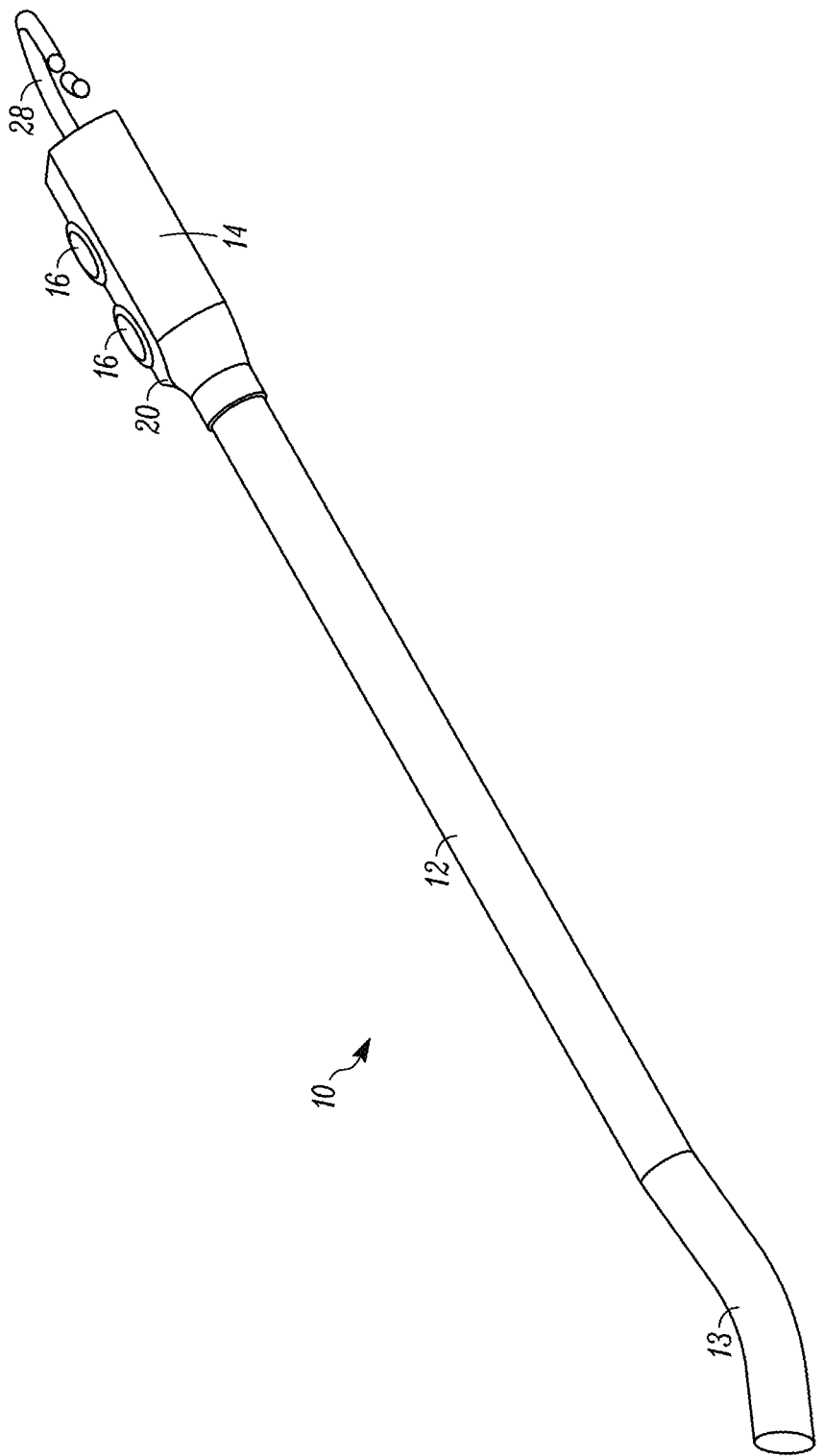
FIGS. 7 and 8 illustrate a perspective view and a perspective cutaway view, respectively, of one example of an endoscope with which the steerable catheter robotic system shown herein may be employed.
Figure 8:
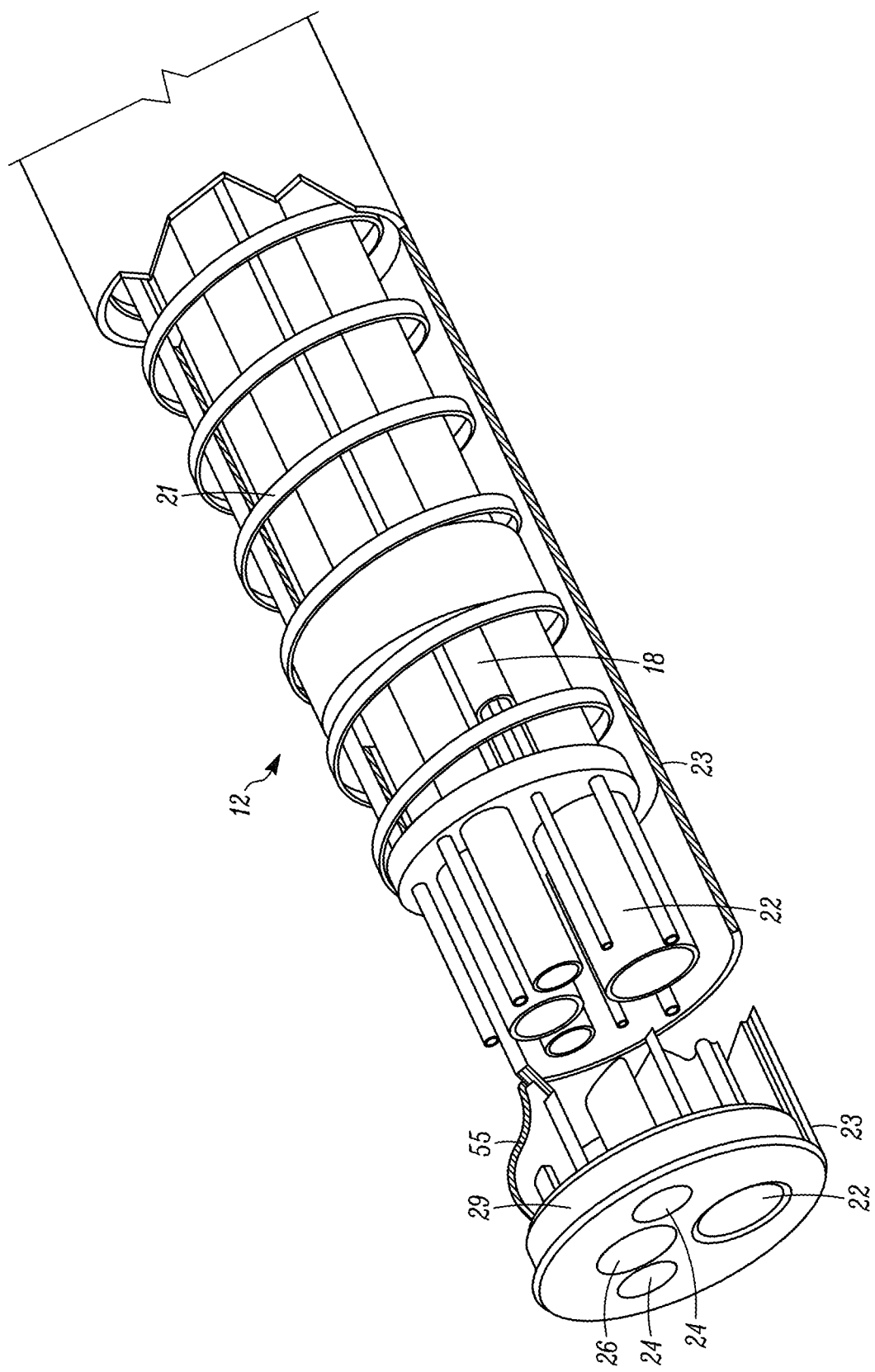

FIGS. 7 and 8 illustrate a perspective view and a perspective cutaway view, respectively, of one example of an endoscope with which the steerable catheter robotic system shown herein may be employed. The endoscope 10 can be used in a variety of medical procedures in which imaging of a body tissue, organ, cavity or lumen is required.

The endoscope 10 includes an insertion tube 12 having a imaging device 26 at its distal end (FIG. 8) and a control handle 14 connected to the insertion tube 12. The insertion tube 12 may be detachable from the control handle 14 or may be integrally formed with the control handle 14. The diameter, length and flexibility of the insertion tube 12 depend on the procedure for which the endoscope 10 is used.

As shown in FIG. 8, the insertion tube 12 has one or more longitudinal channels 22 through which an instrument can reach the body cavity to perform any desired procedures. One of the channels 22 can be used to deliver the steerable flexible catheter described herein. The insertion tube 12 may be steerable or have a steerable distal end region 13 (FIG. 7). The insertion tube 12 also may have control cables 18 (FIG. 8) for the manipulation of the insertion tube 12. The control cables 18 are symmetrically positioned within the insertion tube 12 and extend along the length of the insertion tube 12. The control cables 18 may be anchored at or near the distal end of the insertion tube 12. The control cables 18 are attached to controls (not shown) in the handle 14. Using the controls, the wires can be pulled to bend the distal end region 13 of the insertion tube 12 in a given direction.

The imaging device 26 at the distal end of the insertion tube 12 may include, for example, a lens, single chip sensor, multiple chip sensor or fiber optic implemented devices. The imaging device 26, in electrical communication with a processor and/or monitor, may provide still images or recorded or live video images. In addition to the main imaging device 26, the distal end of the insertion tube 12 may include one or more light sources 24, such as light emitting diodes (LEDs) or fiber optical delivery of light from an external light source.

As shown in FIG. 8, the insertion tube 12 may include a flexible ribbon coil 21 and a flexible sheath 23 that is used to protect the internal components of the insertion tube 12, such as the channels 22, wires and cables 18, from the environment of the body. The end cap 29 of the insertion tube 12 seals the open end of the sheath 23 to close the distal end of the insertion tube 12. The end cap 29 includes an exit port for the channel 22 and peripheral metal posts or sockets (not shown) to which the wires of the control cables 18 are attached.

As shown in FIG. 7, the control handle 14 may include one or more control knobs 16 that are attached to control cables 18 (FIG. 2) for the manipulation of the insertion tube 12. The control handle 14 has one or more ports and/or valves 20 for controlling access to the channels 22 (FIG. 8) of the insertion tube 12. One of the ports may be used for the insertion of the steerable robotic catheter described herein.

Figure 9:
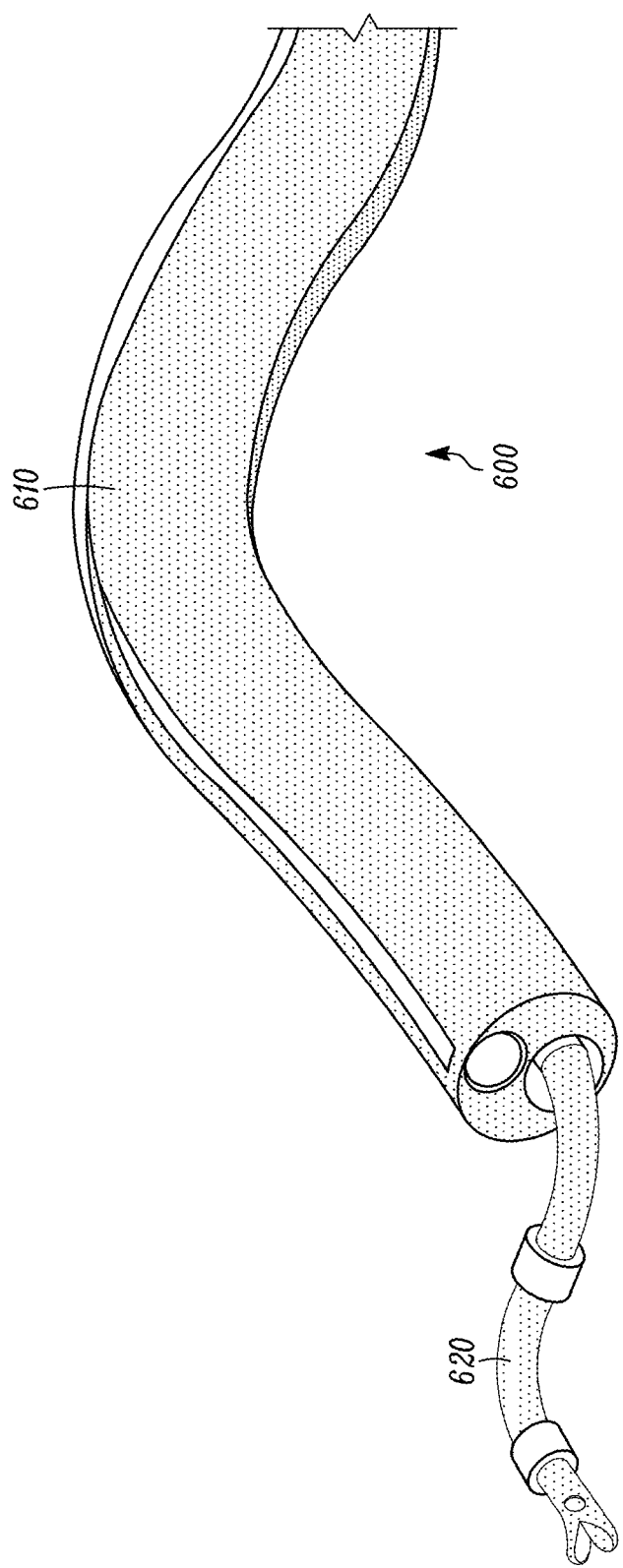
FIG. 9 shows one example of a surgical arrangement that includes an endoscope and the steerable catheter robotic system.

FIG. 9 shows one example of a surgical arrangement 600 that includes an endoscope and the steerable catheter robotic system. The figures show the insertion tube 610 of the endoscope through which the distal end 620 of steerable catheter robotic system is visible.

Figure 10:
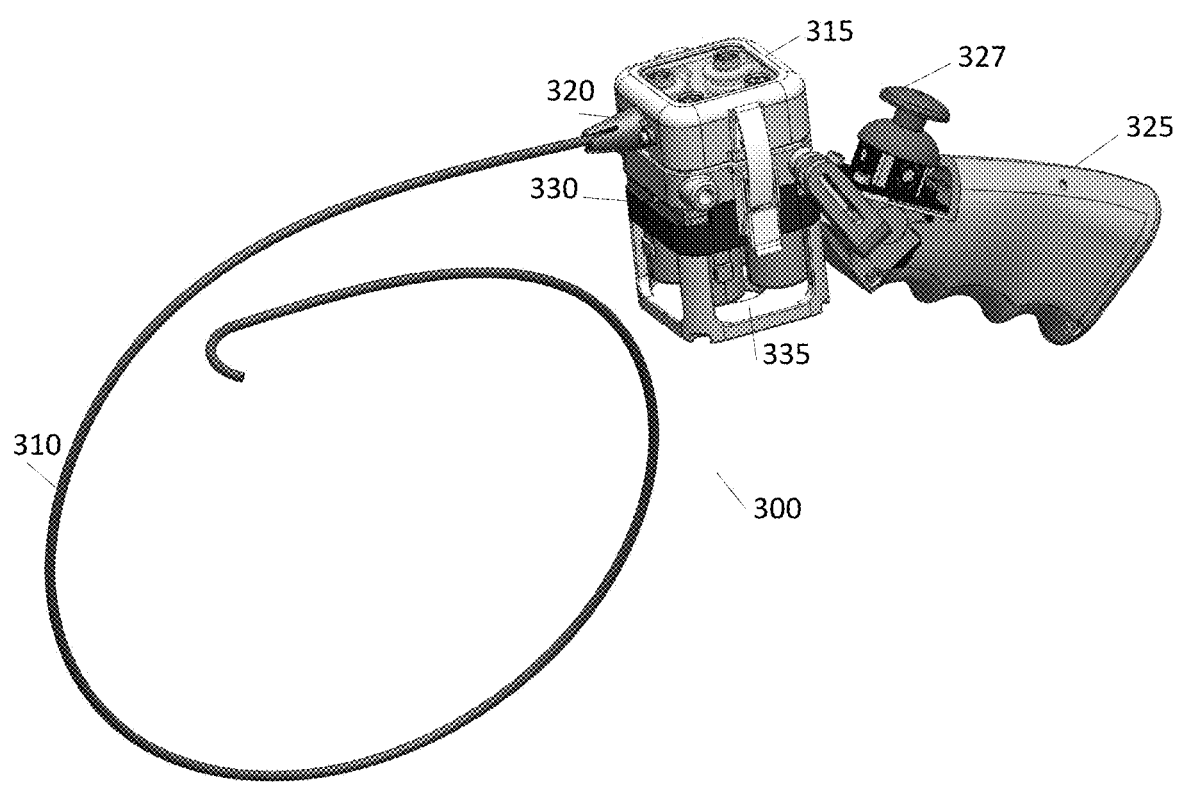
FIG. 10 shows one example of the overall handheld, steerable robotic catheter system.

FIG. 10 shows one example of the overall steerable robotic catheter system 300 that includes catheter 310, which is connected at its proximal end to the shaft mount 320 of pulley housing assembly 315, and catheter handle 325, which includes a finger-controlled (e.g., thumb-controlled) joystick 327. While the catheter handle 325 can assume different shapes, in some embodiments a catheter handle 325 may include an elongated segment that is shaped for convenient grasping with one hand, with the joystick 327 situated towards one end of the elongated segment and arranged so that all of the available controls included with the joystick are accessible and manipulatable with the movement of a single finger (e.g., the thumb) of the grasping hand. In this way the joystick can be placed in any pivotable position by the user's thumb or other finger. The grasping segment of the handle 325 may have a length and cross section sufficiently sized to permit convenient grasping by at least the index and middle fingers. Of course, in alternative embodiments the shape and size of the catheter handle 325 as well as the location of the finger-controlled joystick 327 may be vary in accordance with various ergonomic considerations.

Figure 14:
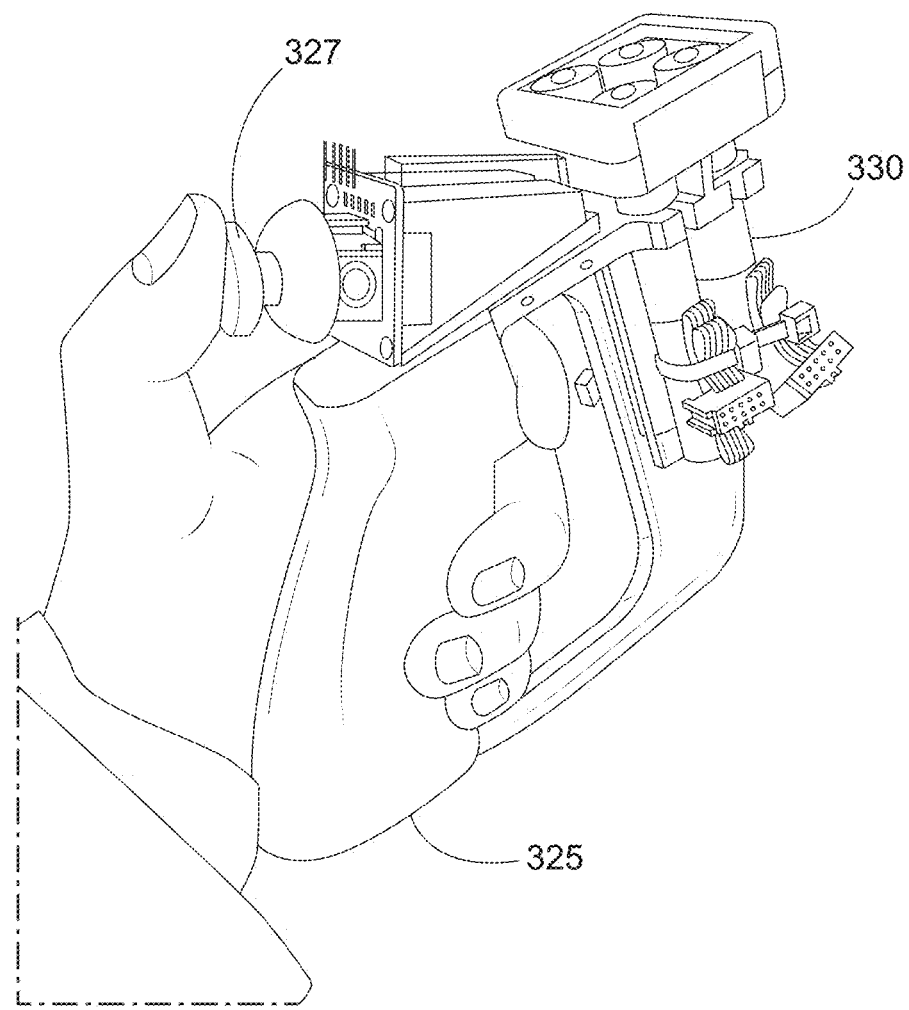
FIG. 14 shows one example of the catheter handle with the motor control unit.

In one embodiment, motor control unit 330 (which includes the pulley housing assembly 315 operatively coupled to the motor control assembly 335) is removably attached to the catheter handle 325. Examples of this embodiment are shown in FIG. 10 as well as in FIG. 14. Any suitable mounting or coupling mechanism such as a clamp, screw thread, clip-fit or the like may be used to secure the motor control unit 330 to the catheter handle 325. For this purpose, in some embodiments the catheter handle 325 may have an adapter to receive the motor control unit 330. The attachment point of the motor control unit 330 on the catheter handle 325 may be determined by various ergonomic considerations such as, for example, to ensure that the weight of the catheter handle 325 is distributed in a way that allows the user to conveniently hold and manipulate the catheter handle 325 and joystick 327.

The joystick 327 on the catheter handle 325 provides the bending angles commands to the processor that interprets those commands and controls the rotation of the motors to pull the articulation wires that marionette the catheter in the desired directions in accordance with the position of the joystick. The mapping between the displacement of the joystick 327 and the displacement of the articulation wires necessary to move the robotic instrument in a certain direction by a certain amount may be accomplished using, for instance, a calibration routine that operates in accordance with inverse kinematics equations such as those described above.

The processor used to control the motors may be located in any suitable location. For instance, it may be co-located with motor control unit 330, contained within the catheter handle 325, or remotely located and connected to the motor control unit 330 by a wired or wireless (Bluetooth) interface.

The calibration between the output movement of the robotic instrument of the catheter and the rotational motions required by the motors is nonlinear. This calibration may be pre-calibrated or learned using an online machine learning technique which tracks the movement of the catheter as it is being used and updates its calibration model. In this adaptive configuration, a method of measuring catheter movement is required. This may be accomplished, for example, by providing an embedded electromagnetic tracker at the catheter tip, or by using computer vision software on the video of the robotic instrument provided by the endoscopic camera to estimate the movement of the robotic instrument. In some cases offline calibration or one-time calibration can be accomplished on a test-rig without requiring embedded sensing.

Figure 11:
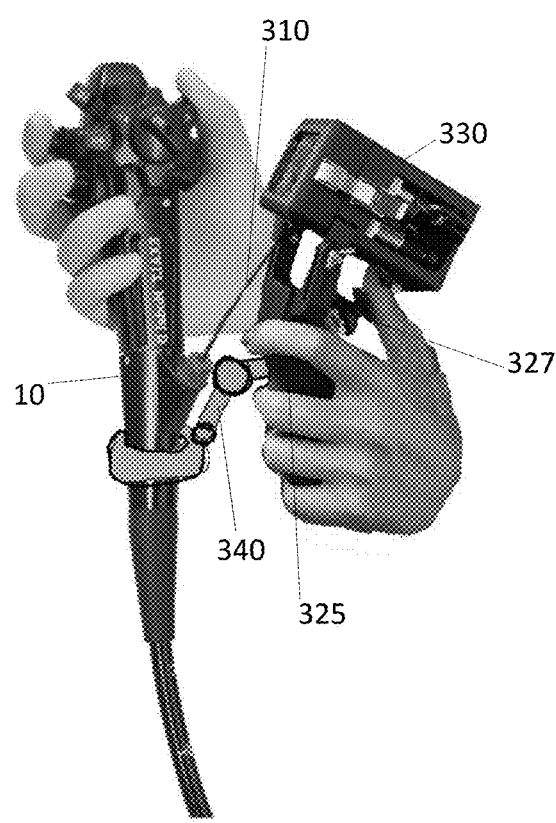
FIG. 11 shows a user holding an endoscope in one hand and the robotic catheter system of FIG. 10 in the other hand.

FIG. 11 shows a user holding an endoscope 10 in one hand and the robotic catheter system of FIG. 10 in the other hand. As shown, the catheter 310 is inserted through the channel port of the endoscope 10. The user is gripping the catheter handle 325 with a single hand while operatively controlling the motion of the catheter instruments using the joystick 327, which in this example is manipulated by the user's thumb. The user holds and manipulates the endoscope 10 using the other hand. In other words, in this example each device is held and controlled using a different hand.

Figure 12:
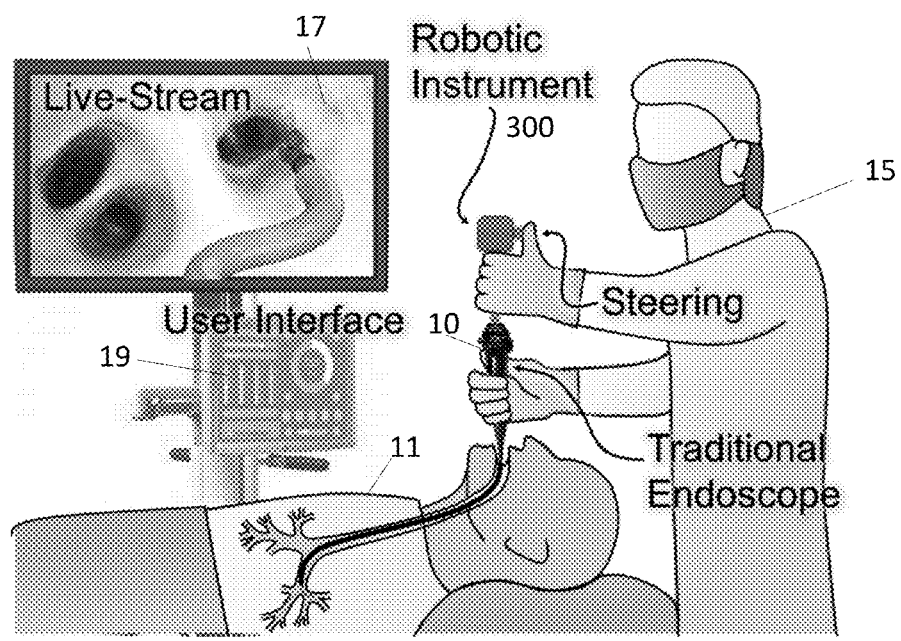
FIG. 12 shows a schematic diagram of a practitioner performing a medical procedure on a patient while holding an endoscope in one hand and the robotic catheter system in the other hand.

FIG. 12 shows a schematic diagram of a practitioner 15 performing a medical procedure on a patient 11 while holding the endoscope 10 in one hand and the robotic catheter system 300 in the other hand. The endoscope 10 include a camera such as described above, which allows the practitioner to view the distal end of the catheter on a video display 17 while performing the procedure. Also shown in FIG. 12 is a user interface 19 (e.g., a touchscreen) that allows the user to set and control various operating parameters of the robotic catheter system 300. The user interface 19 communicates with the processor that controls the motors in the motor control unit 330.

Figure 13:
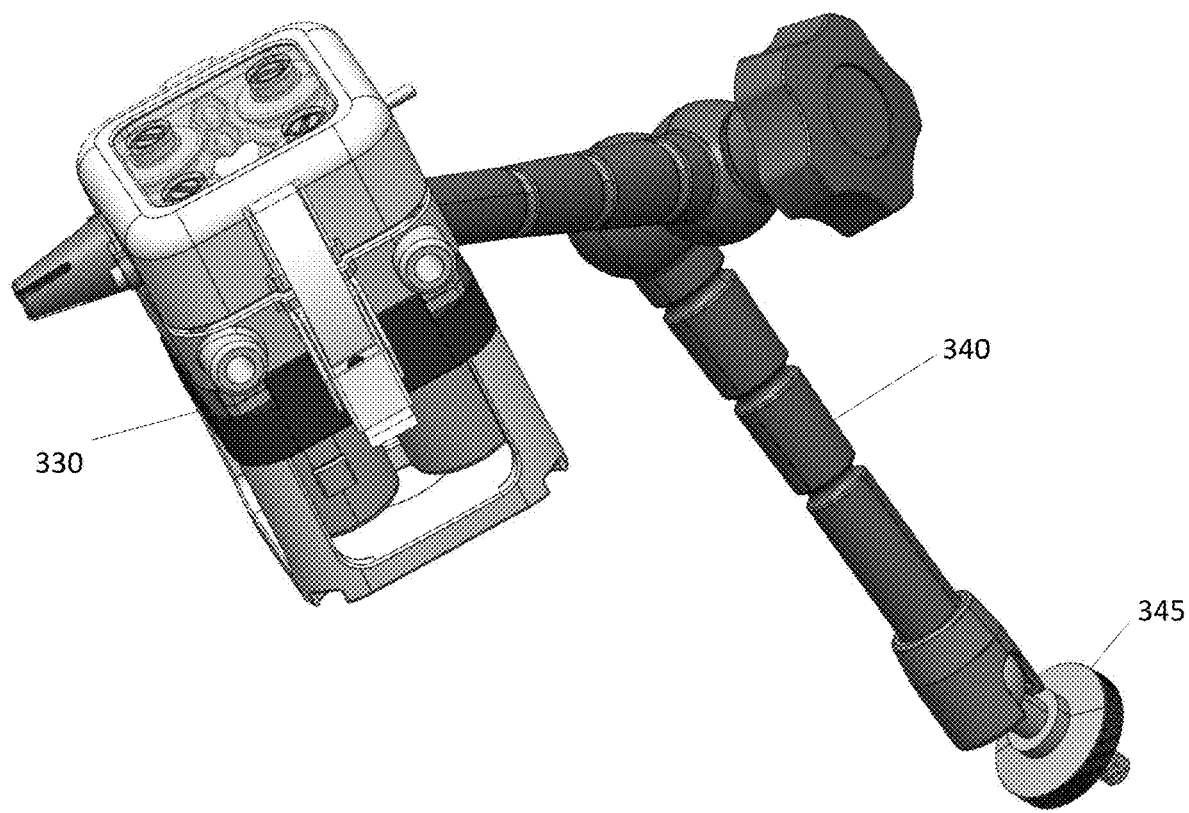
FIG. 13 shows one example of an articulated arm that may be used to secure the robotic catheter system to an endoscope.

In some embodiments the catheter handle may be removably secured to the endoscope using, by way of example, an articulated arm 340, an example of which is shown in FIG. 13. In this example the articulated arm 340 has a connector element for attachment to the endoscope. In the example, of FIG. 13, the connector element is a ball joint 345 to allow for a pivotable connection. However, other types of connectors may be used such as a clamp or the like instead. FIG. 11 shows the catheter handle being secured to the endoscope using the articulated arm. This arrangement provides a significant advantage because it allows a single user to be able to drive and control the endoscope with one hand while simultaneously holding and manipulating the robotic catheter system in the other. Undocking the robotic catheter system from the endoscope allows for multi-user applications. Furthermore, in some applications, the robotic catheter system may be docked or tethered to a platform, staging device, rack or other component instead of being secured to the endoscope.

In an embodiment of the invention, the user may be able to change the mapping between the displacement of the joystick 327 and the displacement of the articulation wires so that, for instance, moving the joystick "up" (i.e., to the 12 o'clock position) may displace the catheter instrument in a different direction as viewed on the display (e.g., video display 17 in FIG. 12). For example, the user may adjust the mapping so that moving up on the joystick may cause the instrument to move to the left or right or in another direction (e.g., 23 degrees-clockwise from "up").

Allowing this relationship between the joystick displacement and instrument displacement to be under user control can provide a number of advantages. For instance, it can be used to correct for any twists on the catheter that may occur at any point along its length while in use, which could prevent displacement of the joystick from matching the displacement of catheter instrument. That is, by way of example, a twist in the catheter may disrupt the user's expectation that moving the joystick to the left will move the image of the catheter on the display to the left. By making this relationship a user-adjustable parameter the user's intuitive expectations can be restored. Any suitable user interface may be provided to adjust this parameter. For instance, in some embodiments the adjustment may be provided on a touchscreen (e.g., touchscreen 17 in FIG. 12) or even on the catheter handle itself. Moreover, for simplicity of use, in some cases the user interface may be provided in the form of a dial (in hardware or as a graphical user interface) that allows the user to easily select the direction in which the robotic instrument should appear to move on the display in response to the displacement of the joystick.

In one embodiment the adjustment of the relationship between the joystick displacement and the instrument displacement may be performed automatically by the processor to ensure that the direction in which the robotic appears to move on the display corresponds to the displacement direction of the joystick. For this purpose the processor will need to receive as input the video signal from the endoscope camera to determine the instrument's direction of motion.

The robotic catheter system described above has a hollow channel that allows multiple different robotic instruments to pass through, making it especially suitable for reuse and flexibility with many different instruments without any modification to the instruments (or the flexible endoscope for that matter). In an alternative embodiment, the catheter (possibly in combination with the pulley housing assembly 500, which may be configured as a disposable cassette so that in some cases the cassette and the catheter may both be disposable) itself serves as the instrument. In this case multiple types of catheter-cassette combinations may be provided, so that instead of having a single multi-instrument catheter, multiple catheters with different instruments are available for use. Thus, there may be provided, for example, one catheter-cassette for laser fibers, another catheter-cassette for biopsy forceps, and so on. Since depending on the particular application there may be certain advantages and disadvantages of having a general-purpose multi-instrument catheter system for passing traditional instrumentation through versus having task-specific catheters that have a sole purpose which address such issues as manufacturability, improved precision, repeatability, sterilizability, cost, reusability, and so, both types of catheters are encompassed by the systems described herein.

In those embodiments in which the catheter is a multi-instrument catheter, the user is provided with a switch or other mechanism (in hardware or software) to toggle between the different instruments so that the joystick may control the operation of any desired ones of the instruments at any given time. Likewise, in those embodiments in which any given instrument has multiple articulating segments, the user is provided with a switch or other mechanism (in hardware or software) to toggle between the different segments so that the joystick may control the operation of any desired segment at any given time.

The handle herein has been described for controlling the operation of a flexible robotic instrument that is designed to pass through the lumen of a catheter. More generally, however, the handle may be employed to control any type of robotic instrument, including flexible robotic instruments such as a robotic arm or the like that do not need to be inserted through a catheter when in use Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. If the specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

The invention claimed is:

1. A steerable catheter robotic system, comprising:
   a catheter removably insertable into an instrument channel of an endoscope, the catheter comprising:
      a flexible outer sheath having a proximal end and a distal end;
      at least one flexible multi-lumen assembly extending through the outer sheath, the multi-lumen assembly having a proximal end and a distal end;
      a robotic instrument for performing a surgical procedure, the robotic instrument being operatively and removably attachable to the distal end of the multi-lumen assembly such that the robotic instrument is teleoperable, the at least one flexible multi-lumen assembly including a plurality of flexible multi-lumen assemblies and the robotic instrument including a plurality of interconnected articulating segments, each of the plurality of flexible multi-lumen assemblies including a plurality of articulation wires for controlling a respective one of the articulating segments;
      a handle operatively and removably attachable to a proximal end of the catheter, the handle being configured for hand-held operation and having a joystick for steering the robotic instrument, the joystick being configured to separately control each of the interconnected articulating segments of the robotic instrument by coordinated operation of the plurality of articulation wires for each of the multi-lumen assemblies to thereby move the robotic instrument in a specified direction; and
   a motor control unit operatively couplable to the proximal end of the at least one multi-lumen assembly for providing rotational movement that imparts translational movement to an actuating arrangement that steers the robotic instrument in accordance with the bending angle commands received from the joystick, wherein the motor control unit is removably attachable to the handle.

2. The steerable catheter robotic system of claim 1 wherein the joystick is configured to issue bending angle commands to thereby teleoperate the robotic instrument.

3. The steerable catheter robotic system of claim 2 wherein the handle is configured to be graspable with a single hand of a user, the joystick being located on a housing so that it is controllable in all pivotable positions using a single finger of the single hand while the handle is being grasped by the single hand.

4. The steerable catheter robotic system of claim 3 wherein the joystick is located on the housing so that it is controllable with a thumb of the single hand of the user.

5. The steerable catheter robotic system of claim 1 wherein each of the articulating segments is operatively and removably attachable to a different one of the multi-lumen assemblies.

6. The steerable catheter robotic system of claim 1 further comprising a processor configured to receive the bending angle commands from the joystick and translate the bending angle commands into rotational movement commands that are provided to the motor control unit to thereby teleoperated the robotic instrument.

7. The steerable catheter robotic system of claim 1 wherein the actuating arrangement includes:
   a plurality of control lumens attached to and surrounding a central lumen to which one of the robotic instruments is removably attached, the plurality of articulation wires for controlling each of the articulating segments extending through a different one of the control lumens.

8. The steerable catheter robotic system of claim 1 further comprising an articulated arm having a first end removably attachable to the handle and a second end removably attachable to a proximal end of the endoscope.

9. The steerable catheter robotic system of claim 1 further comprising a user interface operatively communicating with the processor for receiving values of user controllable parameters.

10. The steerable catheter robotic system of claim 9 where one of the user controllable parameters adjusts a mapping between the bending angle commands from the joystick and the rotational angle commands provided to the motor control unit to thereby adjust a direction in which the robotic instrument appears to move on a display in response to displacement of the joystick in a specified direction.

11. A surgical arrangement, comprising:
   an endoscope having an insertion tube with an imaging system displaced on its distal end and at least one instrument channel extending therethrough;
   a catheter removably insertable into the instrument channel, the catheter comprising:
      a flexible outer sheath having a proximal end and a distal end;
      at least one flexible multi-lumen assembly extending through the outer sheath, the multi-lumen assembly having a proximal end and a distal end;
      a robotic instrument for performing a surgical procedure, the robotic instrument being operatively and removably attachable to the distal end of the multi-lumen assembly such that the robotic instrument is teleoperable, the at least one flexible multi-lumen assembly including a plurality of flexible multi-lumen assemblies and the robotic instrument including a plurality of interconnected articulating segments, each of the plurality of flexible multi-lumen assemblies including a plurality of articulation wires for controlling a respective one of the articulating segments; and a handle operatively and removably attachable to a proximal end of the catheter, the handle being configured for hand-held operation and having a joystick for steering the robotic instrument, the joystick being configured to separately control each of the interconnected articulating segments of the robotic instrument by coordinated operation of the plurality of articulation wires for each of the multi-lumen assemblies to thereby move the robotic instrument in a specified direction;

a motor control unit operatively couplable to the proximal end of the at least one multi-lumen assembly for providing rotational movement that imparts translational movement to an actuating arrangement that steers the robotic instrument in accordance with the bending angle commands received from the joystick, wherein the motor control unit is removably attachable to the handle.

12. The surgical arrangement of claim 11 wherein the joystick is configured to issue bending angle commands to thereby teleoperate the robotic instrument.

13. The surgical arrangement of claim 12 wherein the handle is configured to be graspable with a single hand of a user, the joystick being located on a housing so that it is controllable in all pivotable positions using a single finger of the single hand while the handle is being grasped by the single hand.

14. The surgical arrangement of claim 13 wherein the joystick is located on the housing so that it is controllable with a thumb of the single hand of the user.

15. The surgical arrangement of claim 11 wherein each of the articulating segments being operatively and removably attachable to a different one of the multi-lumen assemblies.

16. The surgical arrangement of claim 11 further comprising a processor configured to receive the bending angle commands from the joystick and translate the bending angle commands into rotational movement commands that are provided to the motor control unit to thereby teleoperate the robotic instrument.

17. The steerable catheter robotic system of claim 16 further comprising a switch associated with the joystick for toggling between each of the interconnected articulating segments of the robotic instrument to select a desired one of the interconnected articulating segments that is controllable by the joystick at any given time.

18. The surgical arrangement of claim 11 further comprising a switch associated with the joystick for toggling between each of the interconnected articulating segments of the robotic instrument to select a desired one of the interconnected articulating segments that is controllable by the joystick at any given time.

* * * * *